US00PP20344P2

(12) United States Plant Patent
Lighty

(10) Patent No.: US PP20,344 P2
(45) Date of Patent: Sep. 22, 2009

(54) ***EPIMEDIUM* PLANT NAMED 'CONALBA'**

(50) Latin Name: *Epimedium hybrida*
Varietal Denomination: Conalba

(75) Inventor: Richard W. Lighty, West Chester, PA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/081,301

(22) Filed: Apr. 14, 2008

(51) Int. Cl.
*A01H 5/00* (2006.01)

(52) U.S. Cl. ..... Plt./429

(58) Field of Classification Search ..... Plt./263, Plt./429
See application file for complete search history.

*Primary Examiner*—Susan B McCormick Ewoldt
(74) *Attorney, Agent, or Firm*—Buchanan Ingersoll & Rooney PC

(57) ABSTRACT

A new *Epimedium hybrida* cultivar is provided that displays a low-growing clumping growth habit. The new cultivar flowers in April and May and forms attractive white blossoms that commonly are borne above the foliage. The plant is well suited for providing distinctive ornamentation when grown in containers, in rock gardens, or as a ground cover. Attractive light green deciduous leaflets are formed. The plant grows well in full sun to moderate shade. During observations to date the new variety has been found to be readily amenable to asexual propagation by division.

1 Drawing Sheet

Botanical/commercial classification: *Epimedium hybrida*/ Bishop's Hat.

Varietal denomination: cv. Conalba.

SUMMARY OF THE INVENTION

The new *Epimedium hybrida* cultivar of the present invention was first discovered during about 1982 as a found seedling in the garden of my home at Kennett Square, Pa., U.S.A. The exact parentage of the new hybrid cultivar is unknown. It is believed that the new plant may be a chance cross of common *Epimedium diphyllum* (non-patented in the United States) and *Epimedium youngianum* 'Niveum' (non-patented in the United States). Such presumed parentage of the new cultivar of the present invention can be expressed as follows:

*Epimeidum diphyllum*×*Epimedium youngianum* 'Niveum'.

The identity of the male parent is not known with certainty.

The new cultivar of the present invention was carefully preserved and has been further studied and evaluated at multiple sites beginning in 1988. Had the new cultivar of the present invention not been discovered and preserved it would have been lost to mankind.

It was found that the new cultivar of the present invention exhibits the following combination of characteristics:

(a) displays a low-growing clumping growth habit,
(b) forms attractive light green deciduous leaflets,
(c) grows well in full sun to moderate shade,
(d) forms attractive white flowers that generally are positioned above the foliage during April and May,
(e) propagates readily by division, and
(f) is well suited for providing distinctive ornamentation when grown in containers, in rock gardens, or as a ground cover.

The new cultivar of the present invention well meets the needs of the horticultural industry and expands the choices of herbaceous perennials, and especially the ornamental ground covers. It performs well in rock gardens, and when grown in containers. The attractive flowers usually are held above the foliage and commonly are displayed during April and May at Eastern, Pennsylvania, U.S.A. The growing requirements for the new cultivar are generally comparable to those of the species. The plant grows well in fertile humus-rich soil with regular adequate but not excessive water. Commonly the plant is cut back in winter before new growth resumes and clumps are divided in the springtime. Approximately 12 months are needed to produce a commercial one-gallon container plant following division.

The new cultivar of the present invention can be readily distinguished from the 'Niveum' cultivar (non-patented in the United States) upon an inspection of the leaves. More specifically, the leaves of the new cultivar are more delicate in appearance.

The new cultivar of the present invention can be readily distinguished from the 'Purple Pixie' cultivar (U.S. Plant Pat. No. 13,966) upon an inspection of the new growth. More specifically, the new cultivar displays green new growth while the new growth of the 'Purple Pixie' cultivar is reddish-purple in coloration.

Division has been used to asexually propagate the new variety at Kennett Square and West Grove, Pa., U.S.A. It has been found that the distinctive combination of characteristics of the new cultivar is firmly fixed and is reliably transmitted to succeeding generations following such division.

The new cultivar has been named 'Conalba' and will be marketed under the ALABASTER trademark.

BRIEF DESCRIPTION OF THE PHOTOGRAPH

The accompanying photograph shows a flowering specimen of the new cultivar in color at an age of approximately four years as nearly true as it is reasonably possible to make the same in a color illustration of this nature. The photograph was taken on Mar. 31, 2005, and shows a typical plant while being grown in a garden setting at Kennett Square, Pa., U.S.A.

DETAILED DESCRIPTION

The following is a detailed description of the new cultivar that was obtained while observing plants having an age of approximately four years during February and March when grown in three-gallon containers at West Grove, Pa., U.S.A., under greenhouse growing conditions. The chart used in the identification color is The R.H.S. Colour Chart of The Royal Horticultural Society, London, England. More common color terms are to be accorded their ordinary dictionary significance.

Botanical classification: *Epimedium hybrida*, 'Conalba'.

Plant:

*Habit.*—Clumping.

*Type.*—Deciduous herbaceous perennial.

*Height.*—Approximately 20 to 25 cm at maturity when in bloom.

*Width.*—Approximately 35 cm. at maturity when in bloom.

*Root system.*—Fine and fibrous.

*Rhizomes.*—The plant spreads in width by rhizomes at a rate of approximately 1 to 2 inches per year. The rhizomes commonly are approximately 1 mm in diameter, possess an internode length of approximately 1 cm, and commonly are between Greyed-Yellow Group 161A and 161B in coloration.

Stems:

*Branching habit.*—Stems arise from rhizomes and typically branch at approximately 7 cm on average. Primary stems will commonly branch into 2 stems with 1, 2, or 3 leaflets and possibly a flowering stem.

*Length.*—Variable, and commonly approximately 5 to 16 cm.

*Shape.*—Substantially cylindrical.

*Texture.*—Generally smooth to the touch and commonly with the presence of light pubescence of less than 1 mm in length on at least some stems.

*Strength.*—Moderate, are capable of remaining substantially upright while supporting the flowers but have a tendency to break when pulled in rough manner.

*Color.*—Greyed-Orange Group 176A.

Leaflets:

*Arrangement.*—Whorled.

*Division.*—Biternate compound leaf.

*Attachment.*—Petiolate for leaves and leaflets.

*Shape.*—Cordate.

*Length.*—Approximately 2 cm when juvenile, and approximately 3 cm when mature.

*Width.*—Approximately 1 cm when juvenile, and approximately 2.5 cm when mature.

*Margins.*—Denticulate.

*Apex.*—Mostly acuminate, and with some more rounded.

*Base.*—Oblique.

*Texture.*—Without pubescence on both surfaces when juvenile and when mature, and possess a satiny upper surface when juvenile and mature.

*Venation.*—Palmate.

*Vein Color.*—When juvenile, leaflets commonly Yellow-Green Group 144C on the upper surface and Yellow-Green Group 144D on the under surface, and on mature leaflets commonly Yellow-Green Group 144B on the upper surface and Yellow-Green Group 145B on the under surface.

*Leaflet color.*—When juvenile commonly Green Group 137C on the upper surface and Green Group 138B on the under surface, and when mature commonly between Yellow-Green Group 146B and 146C on the upper surface and between Yellow-Green Group 144A and 144B on the under surface.

*Petioles.*—Commonly approximately 6 cm in length, approximately 1.5 mm in diameter, and near Greyed-Red Group 179C in coloration.

*Petiolules.*—Commonly approximately 3 to 5 cm in length and approximately 1.5 mm in diameter.

Inflorescence:

*Type.*—Compound panicle.

*Flowering time.*—April and May.

*Bud shape.*—Globular.

*Bud size.*—Commonly approximately 4 mm in diameter and in length.

*Bud texture.*—Smooth.

*Bud apex.*—Obtuse.

*Bud color.*—Yellow-Green Group 144C with Greyed-Yellow Group 160C.

*Flower shape.*—Typical to that of a Bishop's Hat plant, there commonly are four flowers that appear to be joined together but are actually separate having an outer grouping of four spaced petals.

*Flower quantity.*—Commonly approximately 200 to 250 per plant during a flowering season when grown in a three-gallon container.

*Flower diameter.*—Commonly approximately 0.8 to 1 cm from sepal tip to sepal tip, and approximately 1.3 to 1.5 cm from spur tip to spur tip.

*Flower depth.*—Commonly approximately 7 mm.

*Flower color.*—Commonly between White Group 155B and 155D.

*Petal number.*—Four and not fused.

*Petal shape.*—Primarily cupped and rounded.

*Petal apex.*—Rounded.

*Petal base.*—Rounded.

*Petal length.*—Commonly approximately 7 mm.

*Petal width.*—Commonly approximately 6 mm.

*Petal color.*—Commonly between White Group 155B and 155D on both surfaces.

*Calcar number.*—Four.

*Calcar size.*—Commonly approximately 4 mm in length and approximately 2 mm in diameter.

*Sepal number.*—Four per individual flower.

*Sepal shape.*—Lanceolate.

*Sepal texture.*—Smooth on both surfaces.

*Sepal margin.*—Entire when dorsal and ventral.

*Sepal apex.*—Acuminate.

*Sepal length.*—Commonly approximately 2 to 2.5 mm.

*Sepal width.*—Commonly approximately 1.5 mm.

*Sepal color.*—Commonly near Greyed-Purple Group 187B.

*Peduncle size.*—Commonly approximately 15 to 20 cm in length, and approximately 2 mm in diameter.

*Peduncle texture.*—Smooth.

*Peduncle color.*—Grey-Brown Group 199A.

*Pedicel size.*—Commonly approximately 1.4 to 2 cm in length, and approximately 1 mm in diameter.

*Pedicel texture.*—Smooth.

*Pedicel color.*—Near Grey-Grown Group 199A.

*Fragrance.*—Very light.

*Stamen number.*—Four.

*Filament color.*—Yellow Group 13C.

*Anther color.*—Yellow Group 13C.

*Pollen color.*—Yellow Group 13C.

*Pistil number.*—One.

*Pistil color.*—Yellow-Green Group 144B.

*Fruit.*—None observed during observations to date.

Development:

*Vegetation.*—Clump-forming.

*Blooming.*—Commonly during April and May.

*Resistance to diseases.*—No particular resistance or susceptibility to diseases has been noted during observations to date.

*Hardiness.*—U.S.D.A. Hardiness Zone No. 7, and possibly Zone No. 6.

*Resistance to pests.*—No particular resistance or susceptibility to pests has been noted during observations to date.

Plants of the new 'Conalba' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Epimedium hybrida* plant that exhibits the following combination of characteristics:

(a) displays a low-growing clumping growth habit, (b) forms attractive light green deciduous leaflets, (c) grows well in full sun to moderate shade, (d) forms attractive white flowers that generally are positioned above the foliage during April and May, (e) propagates readily by division, and (f) is well suited for providing distinctive ornamentation when grown in containers, in rock gardens, or as a ground cover;

substantially as illustrated and described.

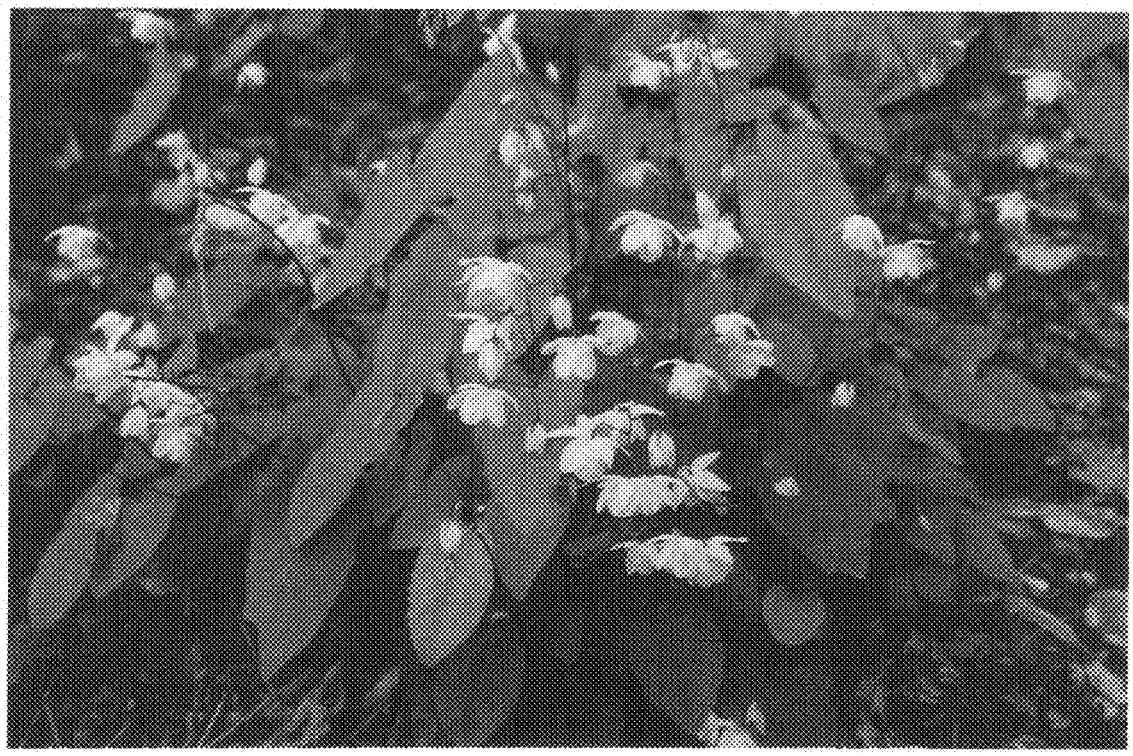

* * * * *